US011504458B2

(12) United States Patent
Crnkovich

(10) Patent No.: US 11,504,458 B2
(45) Date of Patent: Nov. 22, 2022

(54) ULTRASONIC AUTHENTICATION FOR DIALYSIS

(71) Applicant: Fresenius Medical Care Holdings, Inc., Waltham, MA (US)

(72) Inventor: Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 630 days.

(21) Appl. No.: 16/594,270

(22) Filed: Oct. 7, 2019

(65) Prior Publication Data

US 2020/0121840 A1 Apr. 23, 2020

Related U.S. Application Data

(60) Provisional application No. 62/746,720, filed on Oct. 17, 2018.

(51) Int. Cl.
*A61M 1/16* (2006.01)
*A61M 1/14* (2006.01)
*G06F 21/31* (2013.01)
*G06F 21/36* (2013.01)

(52) U.S. Cl.
CPC ............ *A61M 1/1601* (2014.02); *A61M 1/14* (2013.01); *A61M 1/1621* (2014.02); *A61M 1/1654* (2013.01); *G06F 21/31* (2013.01); *G06F 21/36* (2013.01); *A61M 2205/12* (2013.01); *A61M 2205/3375* (2013.01); *A61M 2205/3569* (2013.01); *A61M 2205/3592* (2013.01); *A61M 2205/502* (2013.01); *A61M 2205/60* (2013.01)

(58) Field of Classification Search
CPC .... A61M 1/14; A61M 1/1601; A61M 1/1621; A61M 1/1654; A61M 2205/12; A61M 2205/3375; A61M 2205/3569; A61M 2205/3592; A61M 2205/502; A61M 2205/60; G06F 21/31; G06F 21/36
See application file for complete search history.

(56) References Cited

U.S. PATENT DOCUMENTS

| | | | |
|---|---|---|---|
| 1,406,372 A | 2/1922 | Grapp | |
| 1,689,432 A | 10/1928 | Hartwig | |
| 2,107,173 A | 2/1938 | Bauer | |
| 2,982,895 A | 5/1961 | Exon | |
| 3,130,289 A | 4/1964 | Katzman et al. | |
| 3,605,783 A | 9/1971 | Pecker et al. | |
| 3,694,625 A | 9/1972 | Cole | |
| 3,738,356 A | 6/1973 | Workman | |

(Continued)

FOREIGN PATENT DOCUMENTS

| | | |
|---|---|---|
| DE | 10204003 | 8/2003 |
| EP | 0034916 | 9/1981 |

(Continued)

OTHER PUBLICATIONS

U.S. Appl. No. 16/933,664, Arrizza, filed Jul. 20, 2020.

(Continued)

*Primary Examiner* — John Kim
(74) *Attorney, Agent, or Firm* — Fish & Richardson P.C.

(57) ABSTRACT

A system for blood treatment can include a dialysis machine and an ultrasonic authentication device connected to the blood treatment machine, the ultrasonic authentication device configured to scan a label and send signals containing label information to the dialysis machine.

11 Claims, 3 Drawing Sheets

(56) References Cited

U.S. PATENT DOCUMENTS

| | | |
|---|---|---|
| 3,762,557 A | 10/1973 | Tudor et al. |
| 3,808,401 A | 4/1974 | Wright et al. |
| 3,987,385 A | 10/1976 | Diller et al. |
| 4,014,319 A | 3/1977 | Favre |
| 4,136,708 A | 1/1979 | Cosentino et al. |
| 4,315,523 A | 2/1982 | Mahawili et al. |
| 4,489,535 A | 12/1984 | Veltman |
| 4,503,706 A | 3/1985 | Kolodjski |
| 4,508,622 A | 4/1985 | Polaschegg et al. |
| 4,613,325 A | 9/1986 | Abrams |
| 4,618,343 A | 10/1986 | Palsulich |
| 4,676,467 A | 6/1987 | Palsulich |
| 4,718,447 A | 1/1988 | Marshall |
| 4,734,198 A | 3/1988 | Harm et al. |
| 4,753,370 A | 6/1988 | Rudick |
| 4,756,330 A | 7/1988 | Tischer |
| 4,756,331 A | 7/1988 | Stegmaier |
| 4,778,451 A | 10/1988 | Kamen |
| 4,808,161 A | 2/1989 | Kamen |
| 4,812,239 A | 3/1989 | Mills |
| 4,826,482 A | 5/1989 | Kamen |
| 4,869,286 A | 9/1989 | Williams et al. |
| 4,895,657 A | 1/1990 | Polaschegg |
| 4,902,282 A | 2/1990 | Bellotti et al. |
| 4,902,877 A | 2/1990 | Grasso et al. |
| 4,941,353 A | 7/1990 | Fukatsu et al. |
| 4,950,134 A | 8/1990 | Bailey et al. |
| 4,967,932 A | 11/1990 | Wiley et al. |
| 4,976,162 A | 12/1990 | Kamen |
| 4,979,639 A | 12/1990 | Hoover et al. |
| 5,002,471 A | 3/1991 | Perlov |
| 5,015,389 A | 5/1991 | Portillo et al. |
| 5,024,756 A | 6/1991 | Stemby |
| 5,058,630 A | 10/1991 | Wiley et al. |
| 5,074,359 A | 12/1991 | Schmidt et al. |
| 5,088,515 A | 2/1992 | Kamen |
| 5,100,554 A | 3/1992 | Polaschegg |
| 5,116,021 A | 5/1992 | Foust et al. |
| 5,121,855 A | 6/1992 | Credle, Jr. |
| 5,141,130 A | 8/1992 | Wiley et al. |
| 5,141,493 A | 8/1992 | Jacobsen et al. |
| 5,146,713 A | 9/1992 | Grafius |
| 5,178,182 A | 1/1993 | Kamen |
| 5,181,631 A | 1/1993 | Credle, Jr. |
| 5,192,000 A | 3/1993 | Wandrick et al. |
| 5,193,990 A | 3/1993 | Kamen et al. |
| 5,211,201 A | 5/1993 | Kamen et al. |
| 5,241,985 A | 9/1993 | Faust et al. |
| 5,252,213 A | 10/1993 | Ahmad et al. |
| 5,300,301 A | 4/1994 | Lakin et al. |
| 5,311,899 A | 5/1994 | Isayama et al. |
| 5,324,422 A | 6/1994 | Collem et al. |
| 5,344,392 A | 9/1994 | Senninger et al. |
| 5,350,082 A | 9/1994 | Kiriakides et al. |
| 5,350,357 A | 9/1994 | Kamen et al. |
| D351,470 S | 10/1994 | Scherer et al. |
| 5,353,837 A | 10/1994 | Faust |
| 5,395,351 A | 3/1995 | Munsch |
| 5,421,208 A | 6/1995 | Packard et al. |
| 5,421,823 A | 6/1995 | Kamen et al. |
| 5,431,626 A | 7/1995 | Bryant et al. |
| 5,437,842 A | 8/1995 | Jensen et al. |
| 5,438,510 A | 8/1995 | Bryant et al. |
| 5,447,286 A | 9/1995 | Kamen et al. |
| 5,474,683 A | 12/1995 | Bryant et al. |
| 5,486,286 A | 1/1996 | Peterson et al. |
| 5,490,447 A | 2/1996 | Giulaino |
| 5,499,741 A | 3/1996 | Scott et al. |
| 5,540,265 A | 7/1996 | Polaschegg et al. |
| 5,570,716 A | 11/1996 | Kamen et al. |
| 5,572,992 A | 11/1996 | Kankkunen et al. |
| 5,583,948 A | 12/1996 | Shibayama |
| 5,616,248 A | 4/1997 | Schal |
| 5,628,908 A | 5/1997 | Kamen et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,642,761 A | 7/1997 | Holbrook |
| 5,713,865 A | 2/1998 | Manning et al. |
| 5,728,949 A | 3/1998 | McMillan et al. |
| 5,741,125 A | 4/1998 | Neftel et al. |
| 5,755,683 A | 5/1998 | Houle et al. |
| 5,757,667 A | 5/1998 | Shannon et al. |
| 5,771,914 A | 6/1998 | Ling et al. |
| 5,772,637 A | 6/1998 | Heinzmann et al. |
| 5,788,099 A | 8/1998 | Treu et al. |
| 5,797,519 A | 8/1998 | Schroeder et al. |
| 5,803,320 A | 9/1998 | Cutting et al. |
| 5,811,581 A | 9/1998 | Piva |
| 5,884,813 A | 3/1999 | Bordonaro et al. |
| 5,887,621 A | 3/1999 | Doll |
| 5,925,011 A | 7/1999 | Faict et al. |
| 5,925,014 A | 7/1999 | Teeple, Jr. |
| 5,938,634 A | 8/1999 | Packard |
| 5,939,644 A | 8/1999 | Hsu |
| 5,960,997 A | 10/1999 | Forsythe |
| 5,967,367 A | 10/1999 | Orsbom |
| 5,989,423 A | 11/1999 | Kamen et al. |
| 5,992,685 A | 11/1999 | Credle, Jr. |
| 5,997,502 A | 12/1999 | Reilly et al. |
| 6,026,847 A | 2/2000 | Reinicke et al. |
| 6,036,680 A | 3/2000 | Horne et al. |
| 6,041,801 A | 3/2000 | Gray et al. |
| 6,042,784 A | 3/2000 | Wamsiedler et al. |
| 6,065,941 A | 5/2000 | Gray et al. |
| 6,067,946 A | 5/2000 | Bunker et al. |
| 6,070,761 A | 6/2000 | Bloom et al. |
| 6,118,207 A | 9/2000 | Ormemd et al. |
| 6,126,831 A | 10/2000 | Goldau et al. |
| 6,164,621 A | 12/2000 | Bouchard et al. |
| 6,165,154 A | 12/2000 | Gray et al. |
| 6,187,199 B1 | 2/2001 | Goldau |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,234,997 B1 | 5/2001 | Kamen et al. |
| 6,251,437 B1 | 6/2001 | Fischbach |
| 6,274,106 B1 | 8/2001 | Held |
| 6,312,589 B1 | 11/2001 | Jarocki et al. |
| 6,316,864 B1 | 11/2001 | Ormerod |
| 6,321,587 B1 | 11/2001 | Demers et al. |
| 6,343,614 B1 | 2/2002 | Gray et al. |
| 6,364,159 B1 | 4/2002 | Newman et al. |
| 6,364,857 B1 | 4/2002 | Gray et al. |
| 6,382,923 B1 | 5/2002 | Gray |
| 6,406,276 B1 | 6/2002 | Normand et al. |
| 6,416,293 B1 | 7/2002 | Bouchard et al. |
| 6,451,211 B1 | 9/2002 | Plester et al. |
| 6,459,175 B1 | 10/2002 | Potega |
| 6,464,667 B1 | 10/2002 | Kamen et al. |
| 6,468,424 B1 | 10/2002 | Donig et al. |
| 6,497,676 B1 | 12/2002 | Childers et al. |
| 6,503,062 B1 | 1/2003 | Gray et al. |
| 6,520,747 B2 | 2/2003 | Gray et al. |
| 6,550,642 B2 | 4/2003 | Newman et al. |
| 6,558,343 B1 | 5/2003 | Neftel |
| 6,564,971 B2 | 5/2003 | Heyes |
| 6,592,542 B2 | 7/2003 | Childers et al. |
| 6,595,944 B2 | 7/2003 | Balschat et al. |
| 6,600,882 B1 | 7/2003 | Applegate et al. |
| 6,604,908 B1 | 8/2003 | Bryant et al. |
| 6,613,280 B2 | 9/2003 | Myrick et al. |
| 6,614,008 B2 | 9/2003 | Tidrick |
| 6,625,824 B1 | 9/2003 | Lutz et al. |
| 6,640,650 B2 | 11/2003 | Matsuzawa et al. |
| 6,648,240 B2 | 11/2003 | Simmons |
| 6,648,845 B1 | 11/2003 | Gotch et al. |
| 6,663,359 B2 | 12/2003 | Gray |
| 6,669,051 B1 | 12/2003 | Phallen et al. |
| 6,669,053 B1 | 12/2003 | Garson et al. |
| 6,685,831 B2 | 2/2004 | Donig et al. |
| 6,702,774 B1 | 3/2004 | Polaschegg |
| 6,709,417 B1 | 3/2004 | Houle et al. |

(56) References Cited

U.S. PATENT DOCUMENTS

| | | |
|---|---|---|
| 6,726,656 B2 | 4/2004 | Kamen et al. |
| 6,729,226 B2 | 5/2004 | Mangiapane |
| 6,745,592 B1 | 6/2004 | Edrington et al. |
| 6,746,514 B2 | 6/2004 | Bedingfield et al. |
| 6,749,403 B2 | 6/2004 | Bryant et al. |
| 6,756,069 B2 | 6/2004 | Scoville et al. |
| 6,764,761 B2 | 7/2004 | Eu et al. |
| 6,792,847 B2 | 9/2004 | Tobin et al. |
| 6,807,460 B2 | 10/2004 | Black et al. |
| 6,808,369 B2 | 10/2004 | Gray et al. |
| 6,814,547 B2 | 11/2004 | Childers et al. |
| 6,845,886 B2 | 1/2005 | Henry et al. |
| 6,860,866 B1 | 3/2005 | Graf et al. |
| 6,869,538 B2 | 3/2005 | Yu et al. |
| 6,911,007 B2 | 6/2005 | Nier et al. |
| 6,925,011 B2 | 8/2005 | Pekny et al. |
| 7,084,769 B2 | 8/2006 | Bauer et al. |
| 7,108,790 B2 | 9/2006 | Collins et al. |
| 7,214,210 B2 | 5/2007 | Kamen |
| 7,223,426 B2 | 5/2007 | Cheng et al. |
| 7,232,059 B2 | 6/2007 | Peebles |
| D556,909 S | 12/2007 | Reihanifam et al. |
| D556,910 S | 12/2007 | Reihanifam et al. |
| D576,281 S | 9/2008 | Reihanifam et al. |
| 7,617,850 B1 | 11/2009 | Domey |
| 7,740,152 B2 | 5/2010 | Hughes et al. |
| 7,878,370 B2 | 2/2011 | Sevcik et al. |
| 8,087,303 B2 | 1/2012 | Beavis |
| 8,330,579 B2 | 12/2012 | Kneip et al. |
| 8,516,902 B2 | 8/2013 | Beavis et al. |
| 8,775,196 B2 | 7/2014 | Simpson et al. |
| 8,870,811 B2 | 10/2014 | Gavin et al. |
| 9,517,296 B2 | 12/2016 | Fulkerson et al. |
| 9,542,578 B2 | 1/2017 | Dattolo et al. |
| 9,614,285 B2 | 4/2017 | Blumberg, Jr. |
| 9,675,743 B2 | 6/2017 | Raiford et al. |
| 9,742,065 B2 | 8/2017 | Blumberg, Jr. |
| 9,800,663 B2 | 10/2017 | Arrizza |
| 9,806,399 B2 | 10/2017 | Blumberg, Jr. |
| 10,129,338 B2 | 11/2018 | Arrizza |
| 10,305,992 B2 | 5/2019 | Arrizza |
| 10,491,678 B2 | 11/2019 | Arrizza |
| 10,532,139 B2 | 1/2020 | Medina et al. |
| 2002/0000793 A1 | 1/2002 | Hanaki |
| 2002/0008032 A1 | 1/2002 | Hayenga |
| 2002/0029804 A1 | 3/2002 | Liorati et al. |
| 2002/0060226 A1 | 5/2002 | Kameyama |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0029451 A1 | 2/2003 | Blair et al. |
| 2003/0085621 A1 | 5/2003 | Potega |
| 2003/0111457 A1 | 6/2003 | Tidrick |
| 2003/0130606 A1 | 7/2003 | Tuck |
| 2003/0136189 A1 | 7/2003 | Luuman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0122353 A1 | 6/2004 | Shahmirian et al. |
| 2004/0135078 A1 | 7/2004 | Mandro et al. |
| 2004/0195190 A1 | 10/2004 | Min et al. |
| 2004/0261624 A1 | 12/2004 | Lassota |
| 2005/0103799 A1 | 5/2005 | Litterst et al. |
| 2005/0113734 A1 | 5/2005 | Brugger et al. |
| 2005/0151422 A1 | 7/2005 | Gilmour |
| 2005/0201200 A1 | 9/2005 | Fleig |
| 2005/0230292 A1 | 10/2005 | Beden et al. |
| 2005/0234381 A1 | 10/2005 | Niemetzer et al. |
| 2005/0242034 A1 | 11/2005 | Connell et al. |
| 2006/0027267 A1 | 2/2006 | Fritze |
| 2006/0044192 A1 | 3/2006 | Egbert |
| 2006/0081653 A1 | 4/2006 | Boland et al. |
| 2006/0195064 A1 | 8/2006 | Plahey et al. |
| 2006/0241550 A1 | 10/2006 | Kamen |
| 2007/0085049 A1 | 4/2007 | Houle |
| 2007/0152829 A1 | 7/2007 | Lindsay et al. |
| 2008/0008609 A1 | 1/2008 | Pate et al. |
| 2008/0054837 A1 | 3/2008 | Beavis et al. |
| 2008/0073610 A1 | 3/2008 | Manning |
| 2008/0204347 A1 | 8/2008 | Alvey et al. |
| 2009/0159612 A1 | 6/2009 | Beavis |
| 2012/0138533 A1 | 6/2012 | Curtis et al. |
| 2012/0203573 A1 | 8/2012 | Mayer et al. |
| 2014/0276376 A1 | 9/2014 | Rohde et al. |
| 2015/0168188 A1 | 6/2015 | Reichart |
| 2016/0109398 A1 | 4/2016 | Fulkerson et al. |
| 2016/0239637 A1 | 8/2016 | Miller et al. |
| 2017/0043089 A1 | 2/2017 | Handler |
| 2017/0050834 A1 | 2/2017 | Beavis et al. |
| 2017/0116508 A1 | 4/2017 | Dattolo et al. |
| 2017/0125879 A1 | 5/2017 | Blumberg, Jr. |
| 2017/0176558 A1 | 6/2017 | Jones et al. |
| 2017/0207536 A1 | 7/2017 | Blumberg, Jr. |
| 2017/0239412 A1 | 8/2017 | Court |
| 2017/0281846 A1 | 10/2017 | Manda et al. |
| 2017/0373394 A1 | 12/2017 | Blumberg, Jr. |
| 2018/0043080 A1 | 2/2018 | Gerber et al. |
| 2018/0053986 A1 | 2/2018 | Blumberg, Jr. |
| 2018/0326138 A1 | 11/2018 | Kalaskar et al. |
| 2020/0068021 A1 | 2/2020 | Arrizza |
| 2020/0114054 A1 | 4/2020 | Medina et al. |
| 2020/0121840 A1 | 4/2020 | Crnkovich |

FOREIGN PATENT DOCUMENTS

| | | |
|---|---|---|
| EP | 0311848 | 4/1989 |
| EP | 0399918 | 11/1990 |
| EP | 0532062 | 11/1995 |
| EP | 0875431 | 11/1998 |
| EP | 0796218 | 7/1999 |
| EP | 1050753 | 11/2000 |
| EP | 1187642 | 3/2002 |
| EP | 1277485 | 11/2006 |
| EP | 1783568 | 5/2007 |
| FR | 2569560 | 3/1986 |
| FR | 2769954 | 4/1999 |
| GB | 2091126 | 7/1982 |
| JP | 2004-93065 | 3/2004 |
| WO | WO 92/11046 | 7/1992 |
| WO | WO 92/18048 | 10/1992 |
| WO | WO 95/11855 | 5/1995 |
| WO | WO 96/25214 | 8/1996 |
| WO | WO 97/00400 | 1/1997 |
| WO | WO 99/37342 | 7/1999 |
| WO | WO 00/57935 | 10/2000 |
| WO | WO 01/83360 | 11/2001 |
| WO | WO 2002/049968 | 6/2002 |
| WO | WO 02/059035 | 8/2002 |
| WO | WO 2004/089441 | 10/2004 |
| WO | WO 2006/036353 | 4/2006 |
| WO | WO 2008/143289 | 11/2008 |
| WO | WO 2009/090354 | 7/2009 |
| WO | WO 2011/066299 | 6/2011 |

(56) References Cited

FOREIGN PATENT DOCUMENTS

WO    WO 2012/041790      4/2012
WO    WO 2016/049542      3/2016

OTHER PUBLICATIONS

Communication from European Patent Office from European Application No. 13/80435.7, dated Feb. 1, 2016, 8 pages.

DePaula et al., "Clinical consequences of an individualized dialysate sodium prescription in hemodialysis patients," Kidney International, 2004, 66:1232-1238.

European Search Report dated Mar. 15, 2013, received in European Patent Application No. 08829307.1, 4 pages.

Gambro®, "DEHP-free cartridge blood sets," ©Nov. 2004, Gambro Inc., Lakewood, CO, 4 Pages.

Gambro®, "Prismaflex™ anticipating critical care needs and taking our innovative response to new heights," ©2004, Gambro Inc., Lakewood, CO, 8 pages.

Gotch et al., "Mechanisms determining the ration of conductivity clearance to urea clearance," Kidney International, 2004, 66(89) :S1-S22, 24 pages.

Liljencranis, "Thermal Anemometers", Amateur Design Report, Jul. 17, 2004, URL <http://fonema.se/anemom/anemom.html>.

Sleep Safe™ Operating Instructions, Fresenius Medical Care, Aug. 2000, 134 pages.

U.S. Appl. No. 29/224,370, filed Feb. 28, 2005, and entitled "Peritoneal Dialysis Cycler".

U.S. Appl. No. 29/224,371, filed Feb. 28, 2005, and entitled "Cassette for Peritoneal Dialysis Cycler".

U.S. Appl. No. 29/224,375, filed Feb. 28, 2005, and entitled "Peritoneal Dialysis Cycler".

Zhou et al., "Impact of sodium and ultrafiltration profiling on haemodialysis-related hypotension," NDT Advance Access published online on Sep. 5, 2006.

ULTRASONIC AUTHENTICATION FOR DIALYSIS

CLAIM OF PRIORITY

This application claims priority under 35 USC § 119(e) to U.S. Patent Application Ser. No. 62/746,720, filed on Oct. 17, 2018, the entire contents of which are hereby incorporated by reference.

TECHNICAL FIELD

This disclosure relates to ultrasonic authentication for dialysis.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood. Generally, HD treatments require disposable items (e.g., tubing sets, fluids, dialyzers, etc) to be connected to the HD machine.

SUMMARY

In one aspect of the invention, a system for blood treatment includes a dialysis machine, and an ultrasonic authentication device connected to the dialysis machine. The ultrasonic authentication device is configured to scan a label using ultrasonic signals and to send identified label information to the dialysis machine.

In another aspect of the invention, a method of operating a dialysis system includes scanning a label with an ultrasonic authentication device connected to a dialysis machine, comparing the label information against stored information to determine whether the label corresponds to a required consumable for the dialysis machine, and instructing the user to proceed or halt setup based on the compared information. The ultrasonic authentication device is configured to scan the label using ultrasonic signals and to send identified label information to the dialysis machine.

Implementations can include one or more of the following features.

In some implementations, the label information includes a lot number, a material description, a sku, an expiration date, a size, and/or a concentration.

In certain implementations, the label information is positioned on a clear label.

In some implementations, the system further includes a consumable having a label configured to be scanned by the ultrasonic authentication device.

In certain implementations, the consumable is a saline bag, a dialyzer, a tubing set, and/or a drug.

In some implementations, the label is positioned on a consumable being installed on the dialysis machine.

Embodiments can include one or more of the following advantages.

The ultrasonic authentication devices described herein can help to ensure that a correct disposable (e.g., solution, drug, fluid line set) is connected to the hemodialysis device. This reduces patient risk caused by user error, expired materials, or incompatible disposables. In addition, the ultrasonic authentication devices described herein are also compatible with various labeling applications (e.g., clear labels, paper labels, and/or solid foil/metal labels.) This versatility helps to provide a user-friendly experience when authenticating labels and helps to reduce the risk of errors by the authentication device.

The details of one or more implementations are set forth in the accompanying drawings and the description below. Other aspects, features, and advantages will be apparent from the description and drawings, and from the claims.

DETAILED DESCRIPTION

In certain aspects, an ultrasonic authentication device can be used to identify information from labels on items used in a dialysis treatment. These items can removeable or connectable to a blood treatment device (e.g., disposables, accessories, fluids, and/or drugs.)

Figure 1:
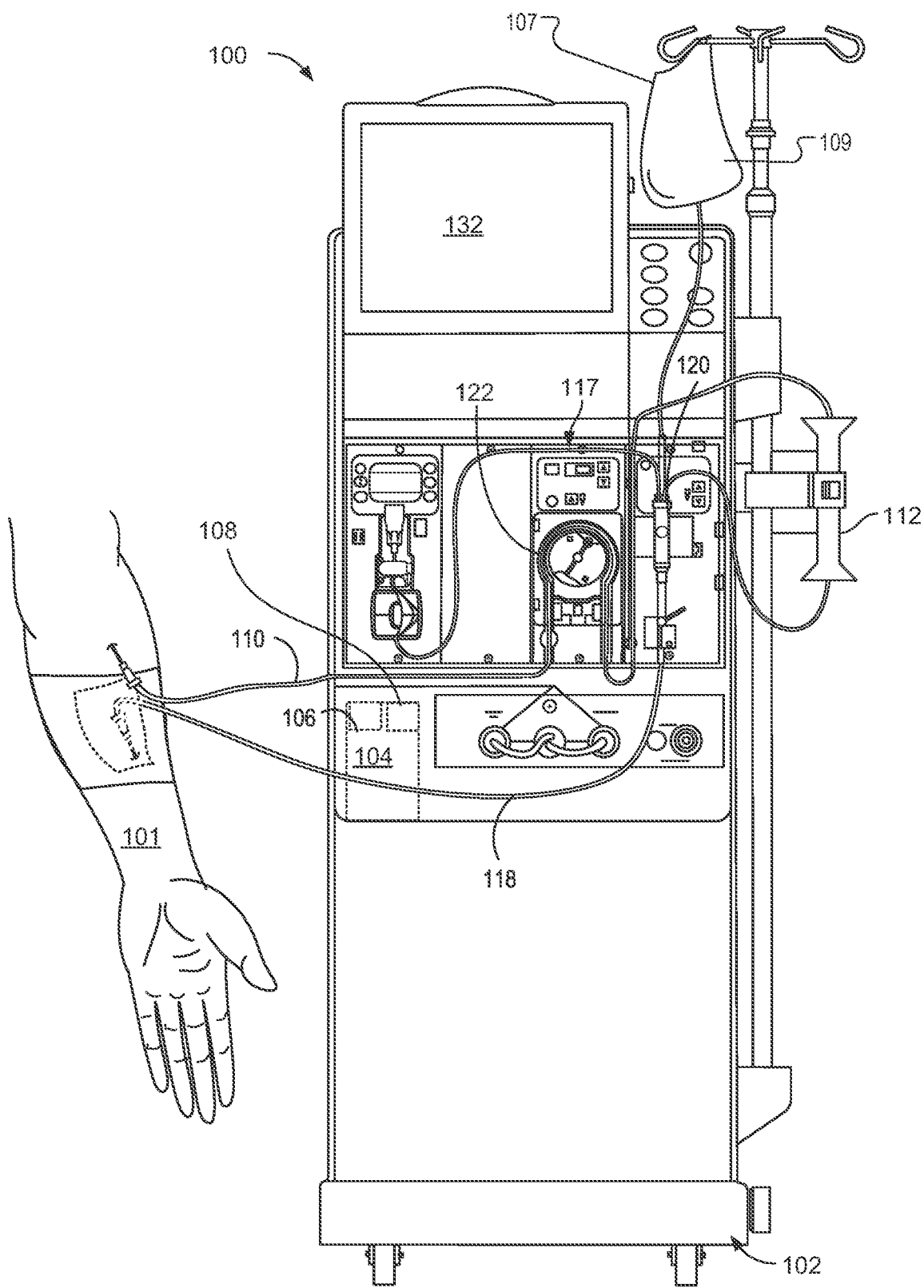
FIG. 1 shows a blood treatment system including a blood treatment machine and an ultrasonic authentication device where the blood treatment machine is configured to identify label information.

FIG. 1 shows a blood treatment system 100 that includes a blood treatment machine (e.g., hemodialysis machine 102) and an ultrasonic authentication device 104, connected to hemodialysis machine 102. The ultrasonic authentication device 104 includes an ultrasonic signal transmitter 106 configured to send ultrasonic signals. An ultrasonic signal receiver 108 is configured to receive reflected ultrasonic signals.

In FIG. 1, the hemodialysis machine 102 and ultrasonic authentication device 104 are connected electronically. A user interface 132 is mounted on or integrated in the hemodialysis machine 102 and is operably controlled by a controller (e.g., a controller 202 shown in FIG. 2) of the hemodialysis machine 102. The user interface 132 can be configured to display information related to the labeling information received by the ultrasonic signal receiver 108. This labeling information can include information related to the function or source of the item (e.g., lot number, description, sku, expiration date, size, and/or concentration.)

In operation, a blood pump 122 of the hemodialysis machine 102 pumps blood through an extracorporeal circuit 117 connected to the hemodialysis machine 102. More specifically, the blood pump 122 draws blood out of a patient 101 via an arterial patient line 118 and forces the blood through a blood chamber of a dialyzer 112. As the blood passes through the blood chamber of dialyzer 112, dialysate passes through a dialysate chamber of the dialyzer 112, so that the blood is cleared of toxins. The cleansed blood then flows through a venous air trap 120 where any air in the blood is collected and is returned to the patient via a venous patient line 110. A saline bag 107 is connected to the venous air trap 120 for introducing saline into the cleansed blood.

In some cases, before identifying the label information, the controller 202 of hemodialysis machine 102 will generate a notification to notify the operator that label information is required. The notification may be visual, auditory, and/or vibrational.

After the ultrasonic authentication is completed, label information is transmitted from the ultrasonic authentication device 104 to hemodialysis machine 102 via the ultrasonic signal transmitter 106 and the ultrasonic signal receiver 108. The ultrasonic signal receiver 108 receives the label information and user interface 132 then optionally displays the label information, an error, and/or further instructions to the user.

Figure 2:
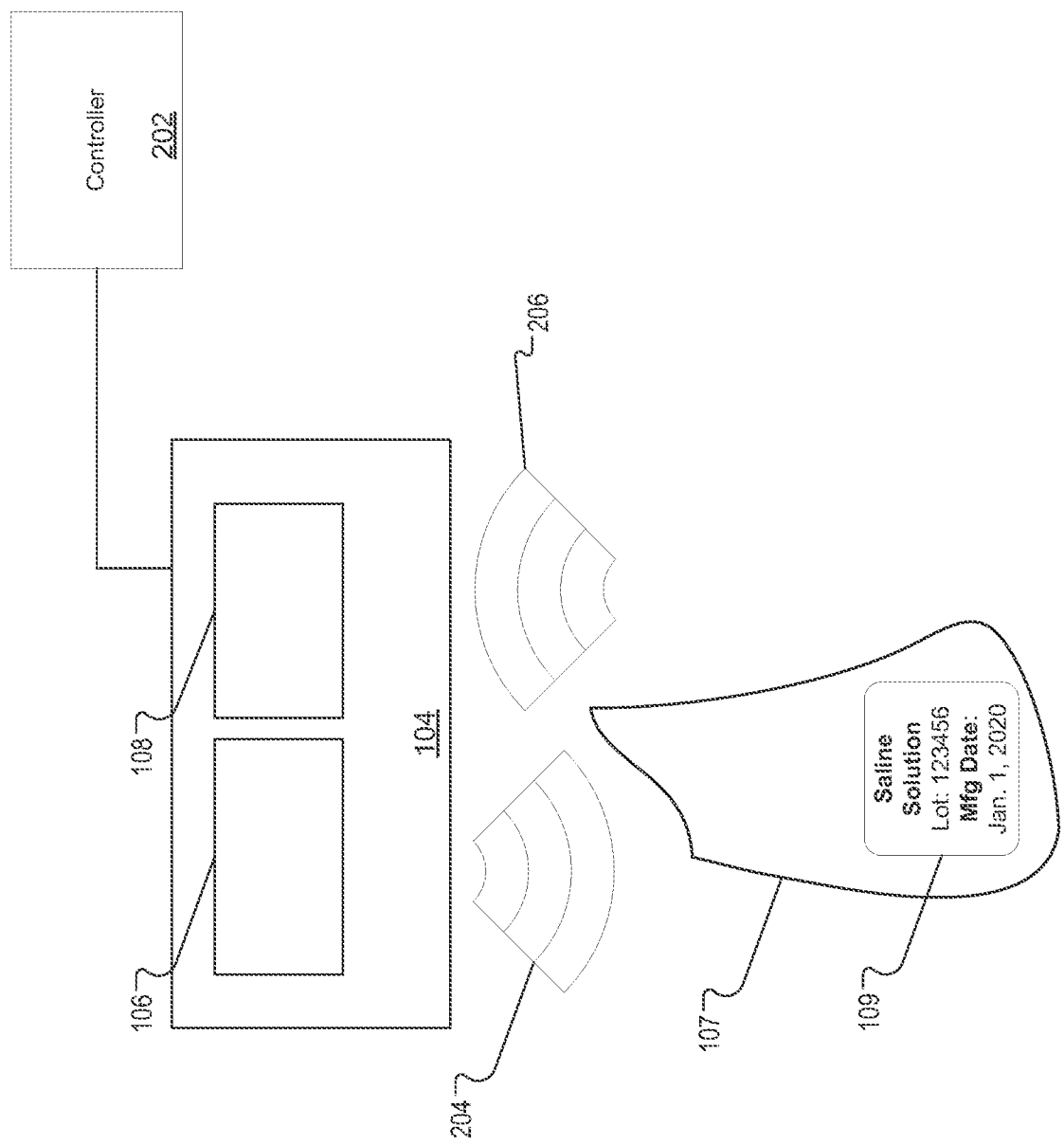
FIG. 2 shows the ultrasonic authentication device of FIG. 1.

FIG. 2 is a schematic illustration of the ultrasonic authentication device 104 including the ultrasonic signal transmitter 106 and the ultrasonic signal receiver 108. The saline bag 107 is an exemplary disposable and includes a label 109. The label 109 can be formed from different labeling applications (e.g., clear labels, paper labels, and/or solid foil/metal labels.) In this example, a user places the bag before the ultrasonic authentication device 104 before use. The ultrasonic authentication device 104 transmits high-frequency sound waves 204 directed at the label 109 and receives reflected waves 206. Based on the reflected waves 206 the controller 202 identifies labeling information from the label 109. In some cases, the received labeling information is displayed to the user on the user interface 132. In other cases, the received labeling information is first compared against expected information. If the information matches expected or acceptable parameters, the treatment or set up is allowed to progress. If the information does not match, the user can be shown an error (e.g., a request to rescan, the reason for rejection, and/or a request to scan a new saline bag.)

Figure 3:
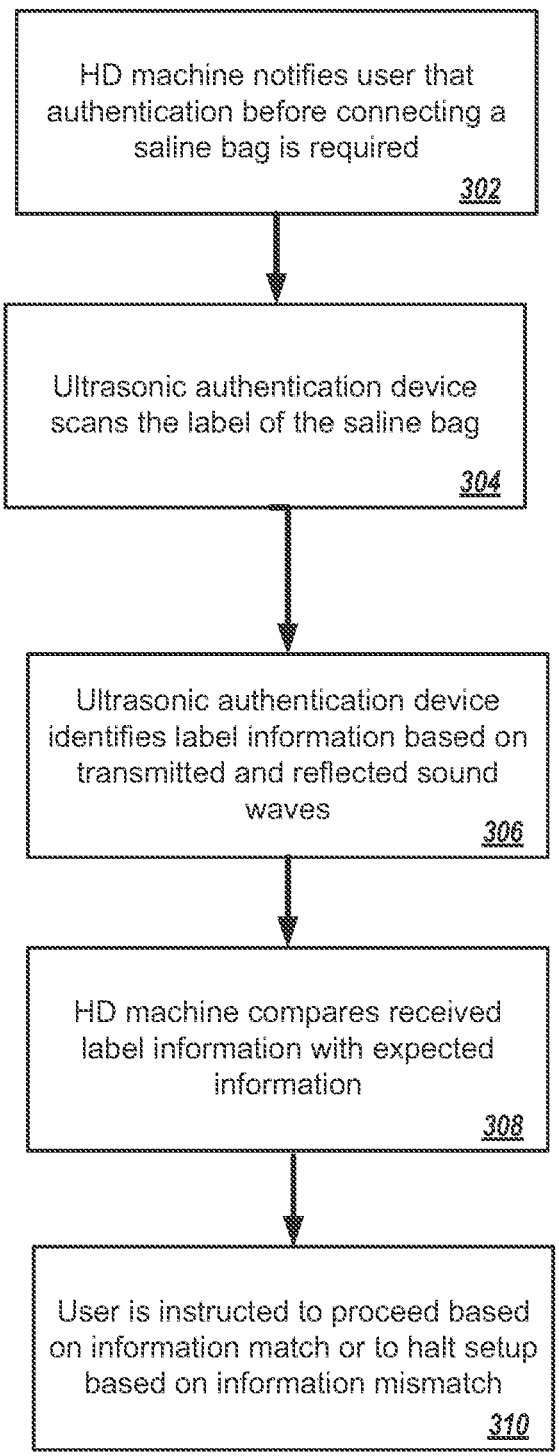
FIG. 3 shows a method of using an ultrasonic identification device in preparation for a dialysis treatment.

FIG. 3 is a flow chart illustrating a method 300 using an ultrasonic identification device in preparation for a dialysis treatment. To prepare for treatment, the hemodialysis machine 102 notifies 304 the user (e.g., via the user interface 132) that authentication is required before connecting a saline bag. Then, the label of the saline bag is scanned 306 by the ultrasonic authentication device when the user places the label near the ultrasonic authentication device. A controller of the HD machine then compares 308 the received label information with expected information. If the label information matches the expected information, the user is instructed to proceed 310 with machine set up. If the information does not match, the user is shown an error (e.g., a request to rescan, the reason for rejection, and/or a request to scan a new saline bag). While FIG. 3 illustrates a method for verifying label information of a saline bag, other connectable components of a dialysis system could be similarly verified.

Alternative Implementations

The examples described herein can be implemented in a variety of ways without departing from the scope of the specification.

While the authentication device 104 is generally shown as part of the hemodialysis machine 102, in some cases, the authentication device could be detachable or connectable to a medical device.

While the saline bag 107 and the label 109 are generally described, labels for other removable components could also be used. For example, a label on the extracorporeal circuit or the dialyzer could be authenticated using the authentication device 104.

Elements of different implementations described herein may be combined to form other implementations not specifically set forth above. Elements may be left out of the structures described herein without adversely affecting their operation. Furthermore, various separate elements may be combined into one or more individual elements to perform the functions described herein.

Various embodiments discussed herein may be combined with each other in appropriate combinations in connection with the system described herein. Additionally, in some instances, the order of steps in a method may be modified, where appropriate. Further, various aspects of the systems described herein may be implemented using software, hardware, a combination of software and hardware and/or other computer-implemented modules or devices having the described features and performing the described functions.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Several implementations have been described. Nevertheless, it will be understood that various modifications may be made without departing from the spirit and scope of the description. Accordingly, other implementations are within the scope of the following claims.

What is claimed is:

1. A system for blood treatment, the system comprising a dialysis machine; and
an ultrasonic authentication device connected to the dialysis machine, the ultrasonic authentication device configured to scan a label using ultrasonic signals and to send identified label information to the dialysis machine.

2. The system of claim 1, further comprising a controller configured to generate a user notification of required label authentication before a treatment begins.

3. The system of claim 1, wherein the label information comprises a lot number, a material description, a sku, an expiration date, a size, and/or a concentration.

4. The system of claim 1, wherein the label information is positioned on a clear label.

5. The system of claim 1, further comprising a consumable having a label configured to be scanned by the ultrasonic authentication device.

6. The system of claim 5, wherein the consumable is a saline bag, a dialyzer, a tubing set, and/or a drug.

7. A method of operating a dialysis system, the method comprising:
scanning a label with an ultrasonic authentication device connected to a dialysis machine, the ultrasonic authentication device being configured to scan the label using ultrasonic signals and to send identified label information to the dialysis machine;

comparing the label information against stored information to determine whether the label corresponds to a required consumable for the dialysis machine; and instructing the user to proceed or halt setup based on the compared information.

8. The method of claim 7, wherein the label is positioned on a consumable being installed on the dialysis machine.

9. The method of claim 7, wherein the label is a clear label.

10. The method of claim 7, wherein the label information comprises a lot number, a material description, a sku, an expiration date, a size, and/or a concentration.

11. The method of claim 7, wherein the consumable is a saline bag, a dialyzer, a tubing set, and/or a drug.

* * * * *